United States Patent
Tamaki et al.

(10) Patent No.: US 6,311,545 B1
(45) Date of Patent: Nov. 6, 2001

(54) ANHYDROUS ZINC ANTIMONATE SEMICONDUCTOR GAS SENSOR AND METHOD FOR PRODUCING THE SAME

(75) Inventors: Jun Tamaki, Ritto-cho; Isao Ota; Hideo Sakata, both of Funabashi, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/265,878

(22) Filed: Mar. 11, 1999

(30) Foreign Application Priority Data

Mar. 11, 1998 (JP) .................................... 10-059430

(51) Int. Cl.[7] .................................................. G01N 27/12
(52) U.S. Cl. ............................................ 73/31.06; 422/88
(58) Field of Search ................................ 73/31.06, 23.2; 422/88

(56) References Cited

U.S. PATENT DOCUMENTS

| | | |
|---|---|---|
| 4,110,247 | 8/1978 | Gower, II et al. . |
| 4,542,640 | * 9/1985 | Clifford ................................ 73/31.06 |
| 5,707,552 | * 1/1998 | Watanabe et al. ................... 252/309 |

FOREIGN PATENT DOCUMENTS

| | | |
|---|---|---|
| 0 686 600 A1 | 12/1995 | (EP) . |
| A-51-132890 | 11/1976 | (JP) .................................... 73/31.06 |
| A-52-21298 | 2/1977 | (JP) . |
| B2-57-11848 | 2/1982 | (JP) . |
| A-60-41536 | 3/1985 | (JP) . |
| B2-61-3292 | 1/1986 | (JP) . |
| A-62-69157 | 3/1987 | (JP) .................................... 73/31.06 |
| A-62-125849 | 6/1987 | (JP) . |
| A-62-182116 | 8/1987 | (JP) . |
| A-1-189553 | 7/1989 | (JP) . |
| A-6-219743 | 8/1994 | (JP) . |
| A-8-15200 | 1/1996 | (JP) .................................... 73/31.06 |

OTHER PUBLICATIONS

Takahata, "Tin Dioxide Sensors—Development and Applications", pp. 39–55.*

Chemical Abstracts, vol. 9, No. 10, Sep. 7, 1998 (1998–09–07), Columbus, Ohio, US; Y. Yamada et al.: *Sensing properties to dilute hydrogen sulfide of zinc antimonate thick film sensor prepared from sol solution*, p. 1334; col. r; XP002124214, *abstract*. & Chem Sens., vol. 14, 1998, pp. 1–4.

Y. Anno et al., *Zinc–oxide based semiconductor sensors for detecting acetone and capronaldehyde in the vapour of consommé soup*, Sensors and Actuators B: Chemical, vol. B25, No. 1/3, Apr. 1995 (1995–04), pp. 623–627, XPOOO532848, ISSN 0925–4005, *Section 2. Experimental procedure*.

N. Jayadev Dayan et al., Effect of film thickness and curing temperature on the sensitivity of ZnO: Sb thick–film hydrogen sensor, Journal Of Materials Science: Materials In Electronics, vol. 8, No. 5, 1997, pp. 277–279, XP000730340, ISSN 0957–4522.

(List continued on next page.)

Primary Examiner—Daniel S. Larkin
(74) Attorney, Agent, or Firm—Oliff & Berridge, PLC

(57) ABSTRACT

A sensor for detecting a gas comprises a gas detecting portion comprising an anhydrous zinc antimonate semiconductor. The sensor for detecting a gas is preferably hydrogen sulfide. A method for producing the sensor for detecting a gas comprising the steps of: mixing a zinc compound with colloidal antimony oxide in a $ZnO/Sb_2O_5$ molar ratio of 0.8 to 1.2; calcining the mixture at 300 to 680° C. and grinding the mixture to form electroconductive anhydrous zinc antimonate powder; preparing a sol of the electroconductive anhydrous zinc antimonate; coating the sol of the electroconductive anhydrous zinc antimonate on a substrate of a device; and heating the substrate at a temperature exceeding 680° C., but below 1,000° C.

4 Claims, 1 Drawing Sheet

OTHER PUBLICATIONS

Database WPI, Section Ch, Week 7725, Derwent Publications Ltd., London, GB; Class J04, AN 1997–00959Y, XPOO2124215, *abstract*.

Maekawa, Tomoki et al., "Improvement of Copper Oxide–Tin Oxide Sensor for Dilute Hydrogen Sulfide", J. Matter. Chem., 1994, vol. 4, pp. 1259–1262.

Yoo, Do Joon et al., "Copper Oxide–Loaded Tin Dioxide Thin Film for Detection of Dilute Hydrogen Sulfide," Jpn. J. Appl. Phys., vol. 34, (1995), pp. L 455–L 457.

Yoo, D. J. Et al., "$H_2S$ sensing characteristics of $SnO_2$ thin film prepared from $SnO_2$ sol by spin coating" Journal of Materials Science Letters, vol. 14 (1995), pp. 1391–1393.

* cited by examiner

F I G.1
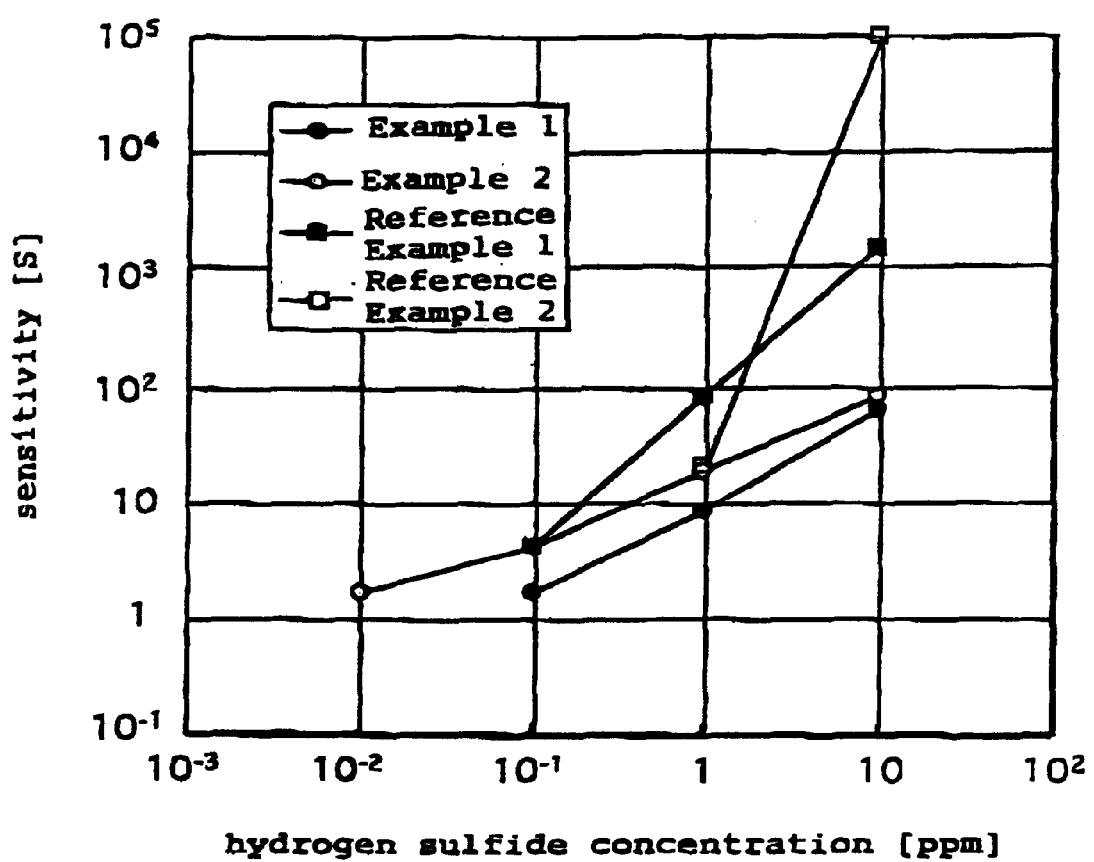

ANHYDROUS ZINC ANTIMONATE SEMICONDUCTOR GAS SENSOR AND METHOD FOR PRODUCING THE SAME

BACKGROUND OF THE INVENTION

1 Field of the Invention

The present invention relates to an anhydrous zinc antimonate semiconductor gas sensor for detecting various reducing gases such as hydrogen sulfide, and to a method for producing the same.

2. Description of the Related Art $SnO_2$ sintered bodies and thin films have been widely put to practical use as a detecting portion of a sensor for various reducing gases, such as hydrogen sulfide, hydrogen, and fuel gases (city gas, propane gas, etc). Japanese Patent Application Laid-open No. Hei 1-189553 describes a thin film sensor having $SnO_2$ and an oxygen activating adsorption catalyst made of a metal, such as Pd, Ru, or the like, simultaneously deposited thereon by sputtering can detect hydrogen gas, methane gas, and the like. In particular, with regard to hydrogen sulfide, JOURNAL OF MATERIALS SCIENCE LETTERS, vol. 14, p. 1391 (1995) describes an $SnO_2$ thin film sensor obtained by heat treatment at 700° C. after spin coating an $SnO_2$ sol; and Jpn. J. Appl. Phys., vol. 34, p. L455 (1995) discloses a thin film sensor comprising an $SnO_2$ thin film obtained by heat treatment at 600° C. after spin coating an $SnO_2$ sol, having carried thereon copper oxide. JOURNAL OF MATERIALS CHEMISTRY, vol. 4, p. 1259 (1994) describes that a sintered sensor comprising an $SnO_2$ sintered body having carried thereon copper oxide shows high sensitivity and high selectivity to $H_2S$ due to its specific high reactivity.

SUMMARY OF THE INVENTION

An object of the present invention is to provide a thin film sensor for detecting hydrogen sulfide at high sensitivity.

As a result of intensive investigation, it has now been found that the above-described object of the present invention can be attained by use of an anhydrous zinc antimonate semiconductor in a detecting portion of a sensor. More particularly, the present invention is to provide a thin film sensor which can detect a gas, for example, hydrogen sulfide at high sensitivity and a method for producing the same, by mixing a zinc compound with colloidal antimony oxide in a $ZnO/Sb_2O_5$ molar ratio of 0.8 to 1.2, coating, for example, dip coating, the resulting electroconductive anhydrous zinc antimonate sol obtained by calcining and grinding the mixture on a substrate of a device, and heating it.

Accordingly, the present invention provides a sensor for detecting a gas, comprising a gas detecting portion comprising an anhydrous zinc antimonate semiconductor Here, the gas is preferably hydrogen sulfide.

Also, the present invention provides a method for producing the above-described sensor for detecting a gas, comprising the steps of:

mixing a zinc compound with colloidal antimony oxide in a $ZnO/Sb_2O_5$ molar ratio of 0.8 to 1.2;

calcining the mixture at 300 to 680° C.;

grinding the calcined mixture to form electroconductive anhydrous zinc antimonate powder;

preparing a sol of the electroconductive anhydrous zinc antimonate;

coating the electroconductive anhydrous zinc antimonate sol on a substrate of a device; and heating the substrate at the temperature above 680° C. but lower than 1,000° C.

The present invention provides a sensor for hydrogen sulfide gas having used anhydrous zinc antimonate semiconductor in a gas detecting portion thereof and a method for producing the same In particular, the anhydrous zinc antimonate semiconductor of the present invention has a sensitivity at least equivalent to that of $SnO_2$ sintered bodies and $SnO_2$ thin films fabricated by sputtering widely put in practical use, and can detect hydrogen sulfide at high sensitivity, even at a hydrogen sulfide concentration of 0.01 ppm. There is no other material that can detect to such a low level of hydrogen sulfide. Therefore, it is useful as a high performance gas sensor for malodorous gas. Further, the present invention enables fabrication of a high performance thin film gas sensor by a coating method, and therefore is low in cost as compared with the production method by deposition.

BRIEF DESCRIPTION OF THE DRAWINGS

In the accompanying drawing;

FIG. 1 is a graph illustrating the sensitivity of hydrogen sulfide gas at a measurement temperature of 300° C. and in a concentration of each hydrogen sulfide gas, with symbols indicating as follows:

● Thin film device fabricated in Example 1

○ Thin film device fabricated in Example 2

■ Thin film device fabricated in Reference Example 1

□ Thin film device fabricated in Reference Example 2

DETAILED DESCRIPTION OF THE INVENTION

The present invention relates to a gas detecting sensor component having anhydrous zinc antimonate in its gas detecting portion. The anhydrous zinc antimonate has semiconducting characteristics That is, the present invention relates to a sensor for detecting a gas which is featured by having anhydrous zinc antimonate having semiconducting characteristics in its gas detecting portion.

In the present invention, the gas which can be detected in the gas detecting portion includes hydrogen sulfide gas.

The anhydrous zinc antimonate having semiconducting characteristics which can be used in the present invention is preferably anhydrous zinc antimonate having electric-conductivity produced by the method described in Japanese Patent Application Laid-open No. Hei 6-219743, further calcined at a specified temperature before it can be used.

According to the method for producing anhydrous zinc antimonate having electric-conductivity, when colloidal zinc antimonate is an antimony oxide sol, it can be produced by mixing and drying the antimony oxide sol and a zinc compound, and then calcining the dry mixture at 300 to 680° C.

The above-described zinc compound may be at least one zinc compound selected from the group consisting of zinc hydroxide, zinc oxide, inorganic acid salts of zinc, and organic acid salts of zinc.

Examples of the inorganic salts of zinc include zinc carbonate, basic zinc carbonate, zinc nitrate, zinc chloride, and zinc sulfate. The organic salts of zinc include, for example, zinc formate, zinc acetate, and zinc oxalate. These zinc compounds may be those commercially available as industrial chemicals. When zinc hydroxide and zinc oxide are used, those having a primary particle diameter of 100 nm or less are preferred. In particular, those zinc salts having acids which are volatile upon calcination, i.e., carbonate, organic acid salts, are preferred. They may be used singly or as a mixture of two or more of them.

The colloidal antimony oxide is antimony oxide having a primary particle diameter of 100 nm or less and includes diantimony pentoxide sol, hexaantimony tridecaoxide sal, hydrated diantimony tetraoxide sol, and colloidal diantimony trioxide. The diantimony pentoxide sol can be produced by known methods, for example, a method in which diantimony trioxide is oxidized (Japanese Patent Publication No Sho 57-11848); a method in which an alkali antimonate is dealkalized with an ion exchange resin (U.S. Pat. No. 4,110,247); a method in which sodium antimonate Is treated with an acid (Japanese Patent Application Laid-open No. Sho 60-41536 and Japanese Patent Application Laid-open No. Sho 62-182116), and the like The hexaantimony tridecaoxide sol can be produced by a method in which diantimony trioxide is oxidized (Japanese Patent Application Laid-open No. Sho 62-125849), while the hydrated diantimony tetraoxide sol can be produced by a method in which diantimony trioxide is oxidized (Japanese Patent Application Laid-open No. Sho 52-21298). The colloidal diantimony trioxide sol can be produced by a gas phase method (Japanese Patent Publication No. Sho 61-3292).

Particularly preferred as the antimony oxide sol which can be used in the present invention is an acid sol having a primary particle diameter of 2 to 100 nm, more preferably 2 to 50 nm, and containing no base, such as an amine or sodium The antimony oxide sol which can be used may contain antimony oxide ($Sb_2O_5$, $Sb_6O_{13}$, or $Sb_2O_4$) in a concentration of 1 to 60% by weight. It can be used as a dry product of antimony oxide sol obtained by, for example, spray-drying, vacuum drying, freeze-drying, or the like. As the above-described colloidal antimony oxide, there may be used commercially available industrial products in the form of diantimony pentoxide sol, diantimony pentoxide powder, or ultrafine diantimony trioxide powder.

The antimony oxide used as a starting material undergoes a slight change in particle diameter when it is calcined together with a zinc compound to be converted into electroconductive anhydrous zinc antimonate, and it is therefore selected so that it has a slightly broader particle diameter range than the particle diameter range of the resulting electroconductive anhydrous zinc antimonate.

When the diantimony pentoxide sol is used as a starting material in the present invention, for example, diantimony trioxide and basic zinc carbonate are dispersed in water in a $ZnO/Sb_2O_3$ molar ratio of 0.01 to 0.2 and the resulting dispersion is reacted with hydrogen peroxide to form a ZnO-doped diantimony pentoxide sol, which can be used as a starting material. Here, the doped ZnO is included in the $ZnO/Sb_2O_5$ molar ratio of 0.8 to 1.2 in the finally obtained, electroconductive anhydrous zinc antimonate.

The mixing of the above-described zinc compound and antimony oxide sol can be carried out using an apparatus such as a SATAKE stirrer, a Fhaudler stirrer, a disper, or the like at a mixing temperature of 0 to 100° C. for 0.1 to 30 hours. The mixing of the above-described zinc compound with a dry product of antimony oxide sol, or colloidal diantinony trioxide can be performed using a mortar, a V type mixer, a Henschel mixer, a ball mill, or the like apparatus.

In the present invention, it is preferred to mix the above-described zinc compound with antimony oxide sol or its dry product, or colloidal antimony sol in a $ZnO/Sb_2O_5$ molar ratio of 0.8 to 1.2. In the present invention, the drying of the mixture (slurry) of the above-described zinc compound and antimony oxide sol can be carried out using a spray drier, a drum drier, a box type hot-air drier, a vacuum drier, a freeze drier, or the like at 300° C. or lower. The slurry may be separated by suction filtration, centrifugation filtration, filter pressing, or the like, or, in some cases, removed of soluble impurities (such as SO, difficult to be volatile upon calcination) originating from the starting material by water-poured cleaning to form a wet cake, which may then be dried at room temperature to 300° C. in a box type hot-air drier or the like. The above-described drying is preferably carried out at 300° C. or lower taking into consideration the apparatus, operation and temperature of subsequent calcination.

In the present invention, the dry product of a mixture of the above-described zinc compound and antimony oxide sol or a mixture of the above-described zinc compound and a dry product of antimony oxide sol or colloidal diantimony trioxide may be calcined at 300 to 680° C. to obtain electroconductive anhydrous zinc antimony ($ZnSb_2O_6$) having a primary particle diameter of 5 to 50 nm. Here, by the term "primary particle diameter" is meant a diameter of a single particle separate one from another but not a diameter of particles which are in an agglomerated form, and can be measured by electron microscopic observation.

In the method for obtaining the electroconductive anhydrous zinc antimonate, after a zinc compound and colloidal antimony oxide are mixed in a $ZnO/Sb_2O_5$ molar ratio of 0.8 to 1.2, the mixture is calcined in a gas containing steam at a temperature of 300 to 680° C., preferably at a temperature greater than or equal to 350° C. but lower than 500° C., and more preferably at a temperature greater than or equal to 400° C. but lower than 500° C., for one half to fifty hours, preferably for two to twenty hours. A temperature of geater, than or equal to 400° C., but lower than 500° C. is most preferred because a sol having a good electric-conductivity and causing less agglomeration can be obtained.

The electroconductive anhydrous zinc antimonate obtained by the above-described method is sintered by calcination to a much lesser extent so that it can easily be ground to 2μm or less by a dry grinding method using a jet-O-mizer, a pin-disk mill, a ball mill, or the like even when it is agglomerated.

By wet grinding the above-described electroconductive anhydrous zinc antimonate in water or an organic solvent using a sand grinder, a ball mill, a homogenizer, a disper, a colloid mill, or the like, an aqueous sol or organic solvent sol can be obtained with ease. Further, it was confirmed that 5 the electroconductive anhydrous zinc antimonate of the present invention was not converted into hydrates but remained anhydrous when ground in water or heated.

In the present invention, a gas detecting device having a detecting portion comprising electroconductive anhydrous zinc antimonate with semiconducting characteristics can be produced by mixing a zinc compound with colloidal antimony oxide in a $ZnO/Sb_2O_5$ molar ratio of 0.8 to 1.2, calcining at 300 to 680° C. and grinding the mixture to form electroconductive anhydrous zinc antimonate ($ZnSb_2O_6$) powder having a primary particle diameter of 5 to 50 nm, preparing a sol of the powder, coating the sol on a substrate of a device, and heating the substrate at a temperature above 680° C., but lower than 1,000° C.

In the present invention, a sensor for detecting a gas can be produced by coating, for example, dipping the above-described electroconductive anhydrous zinc antimonate sol on an alumina substrate on which gold interdigital electrodes are provided and then heating the alumina substrate at a temperature exceeding 680° C., but lower than 1,000° C. Dipping can be carried out by a method including submerging the above-described substrate in the anhydrous zinc antimonate sol and drawing up the substrate.

In the present invention, when the temperature of heat treatment is above 680° C., but lower than 1,000° C., the coating film of anhydrous zinc antimonate has a resistance by two digits or more as high as that before heating, and it comes to have semiconducting characteristics Then, the electroconductive anhydrous zinc antimonate particles having a primary particle diameter of 5 to 50 nm undergo fusion between the particles so that grains grow to 50 to 150 nm. This is accompanied by generation of cavities of 50 to 200 nm In the coating film on the substrate, which facilitates passing of a gas through the coating film so that the sensitivity of detecting a gas can be increased.

On the other hand, when the heat treatment temperature does not exceed 680° C., the coating film of anhydrous zinc antimonate has a resistance as low as 200 to 500 Ω and, hence, electron concentration is too high, resulting in a poor detecting sensitivity since no response is obtained when a small number of electrons migrate. In addition, the electroconductive anhydrous zinc antimonate particles having a primary particle diameter of 5 to 50 nm do not grow substantially so that the resulting coating layer is a dense layer having only a small amount of cavities of a size of 10 nm or less, thus making it difficult for a gas to pass therethrough and, hence, decreasing gas detection sensitivity.

The heat treatment temperature grater than or equal to 1,000° C. is not preferable since the gold of the interdigital electrodes will melt.

In the present invention, the concentration of the electroconductive anhydrous zinc antimonate is 8 to 60% by weight, preferably 10 to 40% by weight. When the concentration of sol is below 8% by weight, the coating film becomes non-uniform to decrease gas detection sensitivity. On the other hand, when the concentration of sol-is above 60% by weight, the thickness of the coating layer of anhydrous zinc antimonate particles becomes too thick for a gas to pass therethrough so that its gas detection sensitivity decreases.

In the method for producing a detecting portion of a sensor for detecting a gas according to the present invention, the above-described zinc compound and colloidal antimony oxide are mixed, and thereafter calcined at 300 to 680° C. to obtain electroconductive anhydrous zinc antimonate. Then, a sol containing the electroconductive anhydrous zinc antimonate is coated on a ceramic (alumina) substrate for a sensor for detecting a gas, and the substrate is calcined at a temperature above 680° C., but below 1,000° C. to impart the anhydrous zinc antimonate ($ZnSb_2O_6$) on the substrate with semiconducting characteristics and at the same time form on the substrate cavity structures suitable for passing a detection gas due to sintering of the anhydrous zinc antimonate particles.

In the above-described production method, when a slurry which consists of a mixture of a zinc compound and colloidal antimony oxide is coated on a substrate and then the substrate is directly calcined at a temperature above 680° C. but below 1,000° C., the anhydrous zinc antimony becomes a non-electroconductive material having no semiconducting characteristics, which is unpreferable, and it is difficult to control particle diameter and cavities so that a proper gas-permeable structural layer cannot be fabricated on the substrate.

EXAMPLES

Hereafter, the present invention will be described in more detail by Examples However, the present invention should not be construed as being limited thereto.

Example 1

Diantimony trioxide (manufactured by Mikuni Smelting Co., Ltd.) (110 kg) and basic zinc carbonate (manufactured by Sakai Chemical Co., Ltd.; $3ZnCO_3 \cdot 4Zn(OH)_2$, containing 70% by weight as ZnO) (860 g) were dispersed in 1,363 kg of water; and 146 kg of 351 hydrogen peroxide and 874 g of 87% by weight formic acid were added to the dispersion, which was heated to 90 to 100° C. and left to react for two hours to obtain a diantimony pentoxide sol. The resulting sol had a specific gravity of 1.168, a pH of 1.85, a viscosity of 1.8 mPa·s, 16.3% by weight as $Sb_2O_5$; a primary particle diameter by transmission electron microscopic observation of 20 to 30 nm, and a BET specific surface area of 30.7 m$^2$/g. The resulting diantimony pentoxide sol (334 kg) was diluted with deionized water to 13.34 by weight as $Sb_2O_5$; and basic zinc carbonate (manufactured Sakai Chemical Co., Ltd.; $3ZnCO_3 \cdot 4Zn(OH)_2$, containing 70% by weight as ZnO) (17.4 kg) was added to the diluted product, followed by stirring for six hours to obtain a slurry. The slurry was 3.1% by weight as ZnO and 12.7% by weight as $Sb_2O_5$, and had a $ZnO/Sb_2O_5$ molar ratio of 0.97. This slurry was dried using a spray drier to obtain powder. The results of X-ray diffraction measurement of the powder indicated that the substance showed a peak which coincided with the peak of hydrated diantimony pentoxide ($Sb_2O_5 \cdot xH_2O$). The dry powder (6 kg) was charged in a 150 mmφ flow calcination furnace and calcined at 595° C. for five hours while introducing into a glass calcination tube a mixed gas having a steam/air partial pressure ratio of 0.30 obtained by bubbling air into a warm bath at 70° C. at a flow rate of two liters/minute. The powder thus obtained was deep blue in color and as a result of X-ray diffraction measurement showed a peak which coincided with that of anhydrous zinc antimonate ($ZnSb_2O_5$). The calcined powder had a BET specific surface area of 47.9 m$^2$/g, a particle diameter of 20.2 nm calculated from the specific surface An article obtained by press-molding the powder at 300 kg/cm$^2$ had an electric-conductivity of 14 Ω by a tester, and a resistivity of 150 Ω·cm by four-probe electric-conductivity measuring apparatus (manufactured by Rollester-Mitsubishi Chemical Co., Ltd.). After the powder was ground using a pin disk, the ground powder (700 g) and water (1,400 g) were charged in a five liter attritor (manufacture by Mitsui Mining Co., Ltd.), and wet-ground for sixteen hours with glass beads (1 to 1.5 mm). After the wet grinding, the glass beads were separated with 5.0 kg of deionized water to obtain 7.0 kg of an aqueous sol of anhydrous zinc antimonate. The aqueous sol thus obtained was concentrated to 2.3 kg using a rotary evaporator. The resulting aqueous sol of anhydrous zinc antimonate was a transparent deep blue and had a specific gravity of 1.347, a pH of 6.9, a viscosity of 3.4 mPa·s, and a $ZnSb_2O_6$ concentration of 30.4% by weight. The sol was stable when left to stand at 50° C. for one month. The sol had a primary particle diameter of 10 to 50 nm by transmission electron microscopic observation, and an average particle diameter of 130 nm by laser scattering particle size distribution measuring apparatus (trade name: Coulter N4, manufactured by Coulter Co.), and an average particle diameter of 80 nm when measured by centrifugal sedimentation (trade name: CAPA-700, manufactured by Horiba Seisakusho Co., Ltd.). A dry product of sol had a BET specific surface area of 48.6 m²/g and a particle diameter of 19.9 nm as calculated from the specific surface area.

On an alumina substrate (9 mm×13 mm×0.4 mm (thickness)) provided with gold interdigital electrodes with a line width of 0.38 mm and a line distance of 0.25 mm was dip-coated the above-described sol. The coated substrate was heated in an electric furnace at 900° C. for four hours to fabricate a thin film device.

The resistance of the coating film of zinc antimonate in the air was 300 Ω before the heat treatment at 900° C., which changed to $10^6$ Ω after the heat treatment at 900° C. Upon scanning electron microscopic observation, the anhydrous zinc antimonate particles grew to 50 to 150 rim in diameter and in accordance therewith a number of cavities of 50 to 200 nm were. observed during the growth of the particles. The thickness of the coating film was 1.0 to 1.5 μm.

Example 2

The same operations as in Example 1 were followed except that the aqueous sol of electroconductive anhydrous zinc antimonate was diluted two-fold with deionized water to change its $ZnSb_2O_6$ concentration to 15.2% by weight and the alumina substrate (9 mm×13 mm×0.4 mm (thickness)) provided with gold interdigital electrodes was dip-coated.

The resistance of the coating film of zinc antimonate in the air was 300 Ω before the heat treatment at 900° C., which changed to $10^7$ Ω after the heat treatment at 900° C. Upon scanning electron microscopic observation, the anhydrous zinc antimonate particles grew to 50 to 150 nm in diameter, and in accordance therewith, a number of cavities of 50 to 200 nm were observed during the growth of the particles. The thickness of the coating film was 0.5 to 0.7 μm Comparative Example 1

The same operation as in Example 1 was followed except that the heat treatment of the coated substrate after dip coating was carried out at 600° C. for four hours.

The resistance of the coating film of zinc antimonate in the air was 300 Ω before the heat treatment at 600° C., which remained at 200 Ω after the heat treatment at 600° C. Upon scanning electron microscopic observation, the anhydrous zinc antimonate particles grew to 10 to 50 nm in diameter and substantially no particle growth occurred. Only a small number of cavities of 10 nm or less were observed.

Comparative Example 2

The same operations as in Example 1 were followed except that the heat treatment after the dip coating was carried out at 1,000° C. for four hours. By scanning electron microscopic observation, molten gold was observed on the anhydrous zinc antimonate particles.

Comparative Example 3

The same operations as in Example 1 were followed except that the aqueous sol of electroconductive anhydrous zinc antimonate was diluted five fold with deionized water to change the $ZnSb_2O_6$ concentration to 6.1% by weight before the alumina substrate could be dip-coated.

Reference Example 1

An alumina substrate (9 mm×13 mm×0.4 mm (thickness)) provided with interdigital electrodes and spin-coated with a 10% by weight tin oxide sol (primary particle diameter: 3 nm) was charged in a box type electric furnace and heat treated at 700° C. for thirty minutes to fabricate a device.

Reference Example 2

The device fabricated in Reference Example 1 was immersed in a mixed solution of a 0.05 mol/liter aqueous $CuCl_2$ solution, a sensitizer, and a 1 mol/liter aqueous $CH_3CO_2NH_4$ solution at 30° C. for twentyfour hours to fabricate a device imparted with 5% by weight as CuO of a sensitizer.

Measurement of Gas Detection Sensitivity

The devices fabricated in Examples 1 and 2, Comparative Examples 1 to 3, and Reference Examples 1 and 2 were measured for their electric resistance Ra in the air at a predetermined temperature and electric resistance Rg in hydrogen sulfide gas at a predetermined temperature, and in a predetermined hydrogen sulfide concentration, and their sensitivity was obtained from Ra/Rg values.

Table 1 shows hydrogen sulfide gas detection sensitivity at a measurement temperature of 350° C. and in a hydrogen sulfide concentration of 40 ppm. In Comparative Example 3, the electric resistance Rg in hydrogen sulfide was too high, accordingly Comparative Example 3 could not indicate the sensitivity.

TABLE 1

| Example 1 | 30 |
| Comparative Example 1 | 1 |
| Comparative Example 2 | 20 |

Table 2 shows hydrogen sulfide gas sensitivity at a measurement temperature of 300° C. and in each hydrogen sulfide gas concentration.

TABLE 2

| Example | Concentration of Hydrogen Sulfide (ppm) | | | |
| --- | --- | --- | --- | --- |
| | 0.01 | 0.1 | 1.0 | 10 |
| Example 1 | — | 1.6 | 8 | 60 |
| Example 2 | 1.6 | 4 | 18 | 80 |
| Reference Example 1 | — | 4 | 80 | 1500 |
| Reference Example 2 | — | — | 20 | $10^5$ |

In Table 2 above, — indicates that no measurement was done since the sensitivity was too low to be measured.

It can be seen that Comparative Example 1 was poor in sensitivity as compared with Example 1.

Thin film sensors fabricated by coating tin oxide sols of Reference Examples 1 and 2, respectively, had very high sensitivities when the concentration of hydrogen sulfide gas was high, but their sensitivity dropped drastically accordingly as the concentration of hydrogen sulfide gas decreased. Much less, the sensitivity at 0.01 ppm, necessary when used as a sensor for malodorous gas, was almost lost. On the other hand, Examples 1 and 2 showed of a less decrease in sensitivity with a change in hydrogen sulfide concentration. In particular, it can be seen that Example 2 shows sensitivity even at 0.01 ppm. This is presumed to be attributable to the fact that in the coating film of Example 2, zinc antimonate particles of 50 to 150 nm in diameter form substantially a single layer so that passage of a gas is improved, which in turn increases sensitivity.

What is claimed is:

1. A sensor for detecting a gas, comprising a gas detecting portion comprising an anhydrous zinc antimonate semiconductor, wherein the anhydrous zinc antimonate has a $ZnO/Sb_2O_5$ molar ratio of 0.8 to 1.2.

2. The sensor for detecting a gas as claimed in claim 1, wherein the gas is hydrogen sulfide.

3. A method for producing the sensor for detecting a gas as claimed in claim 1, comprising the steps of:

mixing a zinc compound with colloidal antimony oxide in a $ZnO/Sb_2O_5$ molar ratio of 0.8 to 1.2;

calcining the mixture at 300 to 680° C.;

grinding the calcined mixture to form electroconductive anhydrous zinc antimonate powder;

preparing a sol of the electroconductive anhydrous zinc antimonate;

coating the sol of the electroconductive anhydrous zinc antimonate on a substrate of a device; and heating the substrate at a temperature above 680° C. but lower than 1,000° C.

4. A method for producing the sensor for detecting a gas as claimed in claim 2, comprising the steps of:

mixing a zinc compound with colloidal antimony oxide in a $ZnO/Sb_2O_5$ molar ratio of 0.8 to 1.2;

calcining the mixture at 300 to 680° C.;

grinding the calcined mixture to form electroconductive anhydrous zinc antimonate powder;

preparing a sol of the electroconductive anhydrous zinc antimonate;

coating the sol of the electroconductive anhydrous zinc antimonate on a substrate of a device; and heating the substrate at a temperature above 680° C. but, lower than 1,000° C.

\* \* \* \* \*